(12) United States Patent
Espinoza et al.

(10) Patent No.: US 6,653,357 B1
(45) Date of Patent: Nov. 25, 2003

(54) METHOD OF MODIFYING AND CONTROLLING CATALYST SELECTIVITY IN A FISCHER-TROPSCH PROCESS

(75) Inventors: Rafael Luis Espinoza, Ponca, OK (US); Terry Shingles, Johannesburg (ZA); Dawid Jakobus Duvenhage, Secunda (ZA); Pieter Lesch Langenhoven, Secunda (ZA)

(73) Assignee: Sasol Technology (Pty) Ltd., Johannesburg (ZA)

( * ) Notice: Subject to any disclaimer, the term of this patent is extended or adjusted under 35 U.S.C. 154(b) by 0 days.

(21) Appl. No.: 09/679,502

(22) Filed: Oct. 4, 2000

(30) Foreign Application Priority Data

Oct. 4, 1999 (ZA) ............................................. 99/6280

(51) Int. Cl.$^7$ .............................................. C07C 27/00
(52) U.S. Cl. ........................ 518/717; 518/715; 518/721
(58) Field of Search ................................. 518/715, 717, 518/721

(56) References Cited

U.S. PATENT DOCUMENTS

| | | | |
|---|---|---|---|
| 4,994,428 A | * 2/1991 | Bell et al. ................... | 502/330 |
| 5,140,049 A | * 8/1992 | Fiato et al. ................. | 518/700 |
| 6,184,431 B1 | * 2/2001 | Slaugh et al. ............... | 585/867 |

OTHER PUBLICATIONS

A.P. Raje et al., "Effect of Potassium Promotion on Iron–Based Catalysts for Fischer–Tropsch Synthesis", J. Catal., 180, 36, (1998).

Dry, M.E. in "Catalysis—Science and Technology" (J. R. Anderson and M. Boudart, Eds), Springer—Verlag Berlin, 1981.

\* cited by examiner

*Primary Examiner*—J. Parsa
(74) *Attorney, Agent, or Firm*—Knobbe Martens Olson & Bear LLP (57) ABSTRACT

The invention provides a method for controlling a selectivity profile of products of a Fischer-Tropsch synthesis process, wherein a catalyst promoter, either dissolved in solution or in a powdered form, is directly injected into the reactor medium, typically into the reactor feedstream. The Fischer-Tropsch process is typically a High Temperature Fischer Tropsch (HTFT) process, and a typical chemical promoter for the HTFT process is potassium. By adding or doping the reaction medium with the catalyst promoter during the synthesis process, the selectivity profile of olefins and paraffins in the product stream is significantly changed, with more olefins being formed whilst the level of paraffins is reduced, and typically the level of olefins in the $C_2$–$C_4$ range is increased. The catalyst promoter may form part of a promoter-carrying compound, for example, potassium carbonate.

8 Claims, 10 Drawing Sheets

FIGURE 9
SAS REACTOR

METHOD OF MODIFYING AND CONTROLLING CATALYST SELECTIVITY IN A FISCHER-TROPSCH PROCESS

This invention relates to a method of modifying and controlling the performance results of a Fischer-Tropsch Synthesis process. Particularly, this invention relates to a modified method of predicting, controlling and thus improving the product selectivity of the High Temperature Fischer-Tropsch synthesis process, and more specifically, the selectivity of the olefinic fraction of the product spectrum.

BACKGROUND OF THE INVENTION

Fischer-Tropsch processes are known to produce gaseous and liquid hydrocarbons as well as oxygenates containing, amongst others, paraffins, olefins, alcohols and aromatics, with a variety of carbon chain length ranges and isomers, which, in general, follow the well-known Anderson-Schulz-Flory distribution. Much emphasis has been placed on the modification endeavors, more particularly to improve, as well as maximize the selectivity of the unsaturated hydrocarbons, especially olefins in the $C_2$–$C_4$ range. whilst maintaining high activity and stability under the normal Fischer-Tropsch synthesis conditions with an iron catalyst. Equation 1 is a general presentation of the Fischer-Tropsch reaction:

$$CO+(1+x)H_2 \tau CH_{2x}+H_2O \qquad (1)$$

The reaction can be carried out in fixed, fluidized or slurry bed reactors. The production of olefins and petrol range products is most favoured by synthesis carried out in a two-phase fluidized bed reactor operating at ~350° C. and 20 bar or higher pressures and utilizing a fused promoted iron catalyst. The fused iron catalyst is typically promoted with alkali chemical and structural promoters. As a result of the high temperatures which are used in these reactors, they are known as High Temperature Fischer-Tropsch (HTFT) reactors, thus distinguishing them from fixed bed and slurry bed reactors (Low Temperature Fischer-Tropsch—LTFT), which operate at temperatures which are about 100–150° C. lower than the said HTFT process.

The HTFT process also utilizes a technique which facilitates online removal of spent catalyst and online addition of fresh catalyst to maintain catalyst activity and selectivity profiles at levels which are as favourable as possible. This technique is aimed at achieving an equilibrium performance and also inhibiting the occurrence of undesirable and negative sudden changes in synthesis performance; thus providing a means through which the product spectrum demands, as dictated by the market forces and downstream requirements, can be met.

The Fischer-Tropsch process is known to be directly influenced by process conditions, for example, feed composition, feedrate, conversion, reaction pressure and temperature. In addition, and particularly for the HTFT process, the chemical composition of the catalyst used in the synthesis process has been shown to have a direct influence on the said product spectrum. Thus the concentration level of the chemical components of the Synthol catalyst matrix, such as sodium, potassium, alumina, silica and the like, has been shown to have a direct correlation with yields and the selectivities of the olefins, paraffins, acids and the oils produced in the process. A number of reports have been published which claim that potassium increases the alkene content of the hydrocarbon products, increases the rate of the water-gas shift reaction and suppresses methane formation.

SUMMARY OF THE INVENTION

The applicant has surprisingly found a method of modifying and controlling, and thus improving, the selectivity profile in favour of the desired Fischer-Tropsch synthesis products. Particularly, the applicant has found a unique method of manipulating, and thus improving, the selectivity profile of the lower olefins produced by means of a High Temperature Fischer-Tropsch process.

The method is characterized in that predetermined amounts of promoter-carrying compound either dissolved in solution or in a powdered form are directly injected into the reactor medium, typically into the reactor feedstream. A typical chemical promoter for the HTFT process is potassium. The applicant has found that by adding or doping the reaction medium with the promoter-containing compound during the synthesis process, the promoter being potassium, the selectivity profile of the olefins and the paraffins in the product stream is significantly changed, with more olefins being formed whilst the level of paraffins is reduced.

Analysis of the iron catalyst sample has surprisingly shown that within the catalyst matrix, potassium is the most mobile component in the solid solution. The Scanning Electron Microscope (SEM), Energy Dispersing X-ray (EDX) and Secondary Iron Mass Spectrometry (SIMS) techniques have convincingly shown that, with time online, a fraction of the potassium promoter continuously migrates away from the iron metal nuclei, to an extent that it is eventually lost altogether from the matrix and is ultimately captured, for example, in the carbon mass deposit that is formed around the catalyst particle during the synthesis process. The applicant has found that the potassium promoter becomes diluted by migration into the mass of the continuously forming elemental carbon around the catalyst particle with time online.

Furthermore, the analysis has surprisingly revealed that the catalyst particles do not contain a homogeneous concentration of the potassium promoter i.e. the amount of potassium contained in the catalyst particles progressively follows a Gaussian trend. Surprisingly, this applies to catalyst particles of the same size. The effect hereof is that some particles have very low levels of $K_2O$. This appears to be an inherent problem which originates from the procedure that is used in the preparation of the catalyst (fusion process).

The applicant has found that when physically adding potassium into a HTFT reactor during the synthesis process, the added potassium replenishes the 'lost' potassium in the catalyst matrix, and in the process the product spectrum becomes more olefinic. The potassium that is added online is in the form of a compound dissolved in solution or in a pulverized state, the compound selected from potassium carbonate and potassium silicate. This added potassium distributes itself homogeneously through all the catalyst particles inside the reactor, boosting those particles which initially contain very little $K_2O$.

The applicant has further found that an expression which combines the concentrations of the previously mentioned catalyst components, known as the selectivity factor, can be successfully used in correlating the selectivities and the yields of the olefins, paraffins, and thus the olefin/paraffin ratios. Previously, such correlations could not be established, so that it was virtually impossible to predict the yield and the selectivity profiles of the Synthol product spectrum. The applicant has also shown that, to a reasonable degree of accuracy, the selectivity levels of the olefins, as compared to the paraffins in the product stream, may be sufficiently predicted based on the amount of potassium added in the solution prepared for injection.

Accordingly, according to a first embodiment of the invention there is provided a method for controlling a selectivity profile of products of a Fischer-Tropsch synthesis process, the method including the step of introducing into a Fisher-Tropsch reaction medium, during the synthesis process, a catalyst promoter or substance, composition or salt containing the catalyst promoter.

The Fischer-Tropsch process is preferably a High Temperature Fischer-Tropsch process, and the catalyst promoter may be introduced into a fluidized bed Fischer-Tropsch reactor feedstream or at any other suitable location.

The catalyst promoter may be a promoter for an iron catalyst. The catalyst promoter may be a Group I element, more particularly the Group I element may be potassium or a salt or compound thereof.

An alkali promoter-containing compound may be used to introduce the catalyst promoter into the feedstream, the promoter-containing compound including an oxide or salts thereof. Typically, the promoter-containing compound is a potassium oxide or a potassium halide. More particularly, the promoter-containing compound may be potassium carbonate, potassium silicate or potassium bromide, preferably potassium carbonate. The promoter-containing compound may be in the form of a solution or a powder.

The selectivity profile of olefins, preferably olefins in the $C_2$–$C_4$ range, may be increased by the addition of the catalyst promoter to the reaction medium during the synthesis process The selectivity factor may relate to the catalyst composition, and conversely the catalyst composition may be determined according to the required selectivity factor. More particularly, the selectivity factor may relate to the potassium oxide, alumina and silica concentrations within the iron catalyst, and even more particularly does not relate to the sodium oxide composition of the catalyst.

The selectivity factor (SF) may be expressed according to the following equation:

$$SF = \frac{(K_2O)}{(Al_2O_3 + SiO_2)} \quad (3)$$

It will, however, be apparent to a person skilled in the art that this is not the only equation which may be used to determine the selectivity factor.

The quantity of additional catalyst promoter required to achieve the desired selectivity factor may be calculated according to the following equation if $K_2CO_3$ is used as the promoter-carrying compound:

$$p = [ReqComp_r x (SiO_2 + Al_2O_3) - K_2O]/0.68 \quad (4)$$

where p is the amount of additional potassium promoter per 100 g Fe;

$SiO_2$, $Al_2O_3$ and $K_2O$ refer to the composition of the spent catalyst to be modified; and ReqComp$_r$ is used to indicate the SF which corresponds to a catalyst with the desired olefin selectivity.

If a compound other than $K_2CO_3$ is used (e.g. $K_2SiO_3$), then the equation should be modified in accordance with the molecular weight of the specific compound.

According to a second embodiment of the invention there is provided a Fischer-Tropsch catalyst system having a desired olefin selectivity factor, the catalyst system including a quantity of catalyst promoter related to the catalyst composition and the selectivity factor.

The catalyst and a catalyst promoter may be substantially as described above. The promoter may be selected from a group including potassium oxide, alumina, silica and sodium oxide.

The selectivity factor may be related to the iron catalyst promoter's potassium oxide, alumina and silica concentrations, and preferably not necessarily to the sodium oxide concentration. The selectivity factor may be determined substantially as described above, as may the quantity of catalyst promoter be determined.

According to yet a further embodiment of the invention there is provided a method of maintaining a selectivity profile of products of a Fischer-Tropsch synthesis process within a preselected range the method including the step of introducing into a Fisher-Tropsch reaction medium, during the synthesis process, a catalyst promoter or substance, composition or salt containing the catalyst promoter.

The method may be the same or substantially similar to the method of modifying and controlling the selectivity profile described above.

DETAILED DESCRIPTION OF THE PREFERRED EMBODIMENTS

It is on the basis of the favourable promotional effects of potassium that an optimum amount thereof is maintained consistently within the catalyst inventory during the synthesis reaction. Under HTFT conditions the iron catalyst particles are known to continuously show the deposition of elemental carbon occurring around them. When carbon is deposited on the iron catalyst is the particles swell arid also disintegrate. In a fluidized catalyst bed in particular, the fines which are produced as a result of catalyst disintegration have a high carbon content and hence have a low particle density. The fine, low density particles are also preferentially lost via cyclones during the synthesis, thereby lowering the available alkali levels even further.

At this stage the potassium is diluted (in terms of $K_2O$ unit volume) inside the catalyst particles, and the amount of potassium that is in contact with iron is lowered. In practice, as the synthesis reaction progresses, the amount of potassium promoter within the catalyst particles gradually diminishes due to the high mobility rate of this particular promoter within the solid solution. As the level of the active potassium within the catalyst matrix progressively decreases, the catalyst itself, complementarily, becomes more selective towards a paraffinic hydrocarbon product. As a result, a desired Fischer-Tropsch product selectivity profile wherein the olefinic fraction is dominant cannot be maintained indefinitely if the diminishing potassium content continuously alters the catalyst effective composition.

The applicant has found a method of continuously maintaining the product yield and selectivity of the HTFT process using an iron-based catalyst, wherein the olefinic product content is dominant. The method of the present invention includes the physical injection of a potassium containing compound, for example potassium carbonate and potassium silicate, into a Fischer-Tropsch fluidized bed reactor feedstream or into the reaction medium at any other suitable location, whilst the process operation is in progress. The injection of the potassium-containing compound is capable of immediately, or substantially immediately, restoring the otherwise declining olefin selectivity levels to the original maximum levels.

The present invention also provides a method for determining, to within a reasonable degree of accuracy, the selectivity levels of the olefins and the paraffins within the hydrocarbon product stream. Previously, it was believed that it was feasible to correlate, with a variable degree of precision, the iron-based Synthol catalyst composition, also known as the catalyst type, with the olefin (and paraffin)

product selectivity. The following expression, which is known as the selectivity factor (SF), combines the concentrations of the promoters and the support components of the iron catalyst:

$$SF = \frac{(K_2O + Na_2O)}{(Al_2O_3 + SiO_2)} \quad (2)$$

wherein each oxide is expressed per 100 g Fe. This factor has traditionally been used, with limited success, as a measurement entity to test whether the hydrocarbon product selectivity profile correlated directly with the catalyst composition. However, it has now been established that the influence of potassium on the selectivity profile is much more pronounced than that of sodium, such that the sodium component concentration, once present in similar amounts to that of potassium, can be excluded from the selectivity factor expression, thereby improving the accuracy of the selectivity factor under these conditions. The new selectivity factor is now expressed as follows:

$$SF = \frac{K_2O}{(Al_2O_3 + SiO_2)} \quad (3)$$

Analysis of the synthesis results shows that there is indeed a direct correlation between the modified selectivity factor and the olefin selectivity as well as the olefin: paraffin selectivity ratios. Expressed differently, if the concentrations of the alumina and silica support components are constant, there exists a direct correlation between the potassium promoter concentration in the catalyst matrix and the olefin selectivity and the olefin: paraffin selectivity ratio. Therefore, a decrease in the amount of active potassium correlates to an increase in selectivity of the paraffinic hydrocarbons, and consequently a decrease in the olefin: paraffin ratio.

By physically injecting an alkali compound containing potassium, such as potassium carbonate or potassium silicate, into a Fischer-Tropsch process operating with a catalyst in a fluidized bed mode, the diminishing catalyst's potassium promoter content is suddenly replenished, and in line with phenomena discussed above, the selectivity profile of the synthesis process is such that the olefin selectivity, and thus also the olefin: paraffin selectivity ratios correspondingly increase. The alkali promoter injection method as herein described is carried out online, and the compound is added either in a solution or a powdered form at a selected injection point to allow mixing with the total feed gas prior to entrance into the reactor. The alkali promoter injection method also increases the synthesis gas conversion capacity. Characteristically, the acids in the reaction water as well as in the unstabilized light oil (ULO) fraction are also increased, whilst the alcohols and the carbonyls remain substantially unchanged.

Furthermore, the process of the present invention, through the results obtained, provides an additional or alternative means of countering negative or poisoning effects of the coal-derived synthesis gas side components, such as sulphur, specifically as regards to the question of catalyst selectivity. The iron catalyst is characteristically sensitive towards the increase in the levels of sulphur as sulphur is preferentially adsorbed onto alkali-rich sites on the catalyst surface thereby rendering them ineffective. Thus if high amounts of sulphur are present in the synthesis gas the catalyst activity and selectivity are severely affected. The present invention, wherein fresh alkali is injected into the catalyst bed, counteracts the negative effects of sulphur poisoning by re-instating the presence of fresh alkali-rich and active sites.

The invention will now be illustrated by means of the following non-limiting examples and with reference to the accompanying figures.

EXAMPLE 1

This example illustrates that a direct online injection of a compound which is a potassium promoter carrier into a Fischer-Tropsch synthesis reactor operating with an iron-based catalyst in a fluidized mode, and under the conditions of the Sasol Synthol process, immediately increases the product olefins and acids selectivities of the process. Furthermore, the injection of the potassium carrier results in a complementary decrease in the paraffin selectivity. This technique was shown to be effective for both the circulating fluidized bed (CFB) reactor and the fixed fluidized bed reactor (Sasol Advanced Synthol (SAS) reactor).

As means of determining the viability of an online promoter addition to a Synthol Fischer-Tropsch reactor, two test runs were conducted on a CFB reactor. 175 kg of potassium carbonate were dissolved in water in order to achieve an estimated increase in the total potassium promoter amount in the reactor by 0.05 g/100 g iron. The overall aim was to monitor the effect which such an online increase of the promoter in the reactor has on the ethylene:ethane ratio in the tailgas of the test reactor.

The injection point includes the preheated total feed to the reactor, comprising fresh synthesis gas feed and internally recycled feed.

Figure 1:
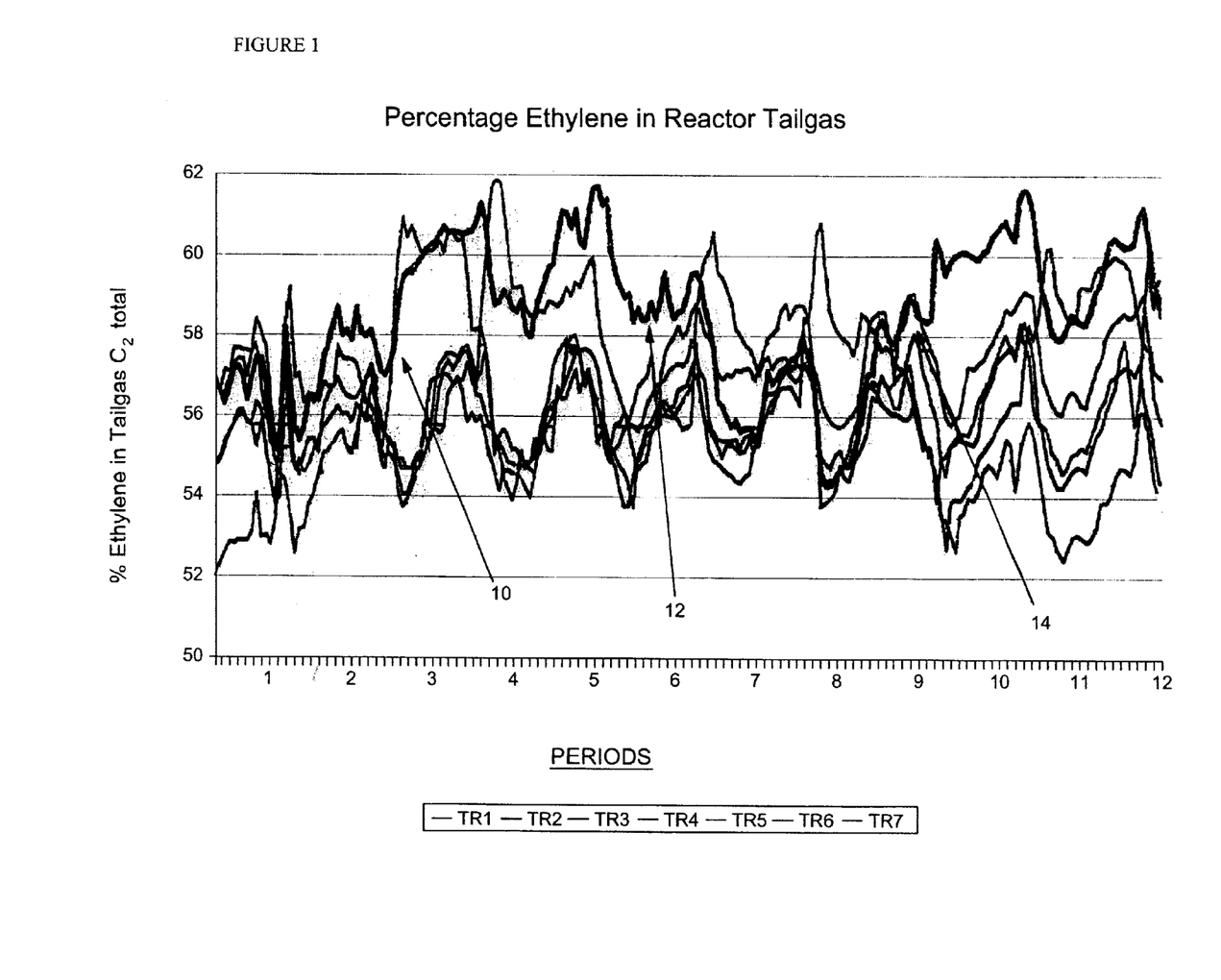
FIG. 1 shows a graphic representation showing the percentage ethylene in reactor tailgas of a Circulating Fluidized Bed reactor when controlling a product selectivity profile of a HTFT process according to the invention.

Referring to FIG. 1, after the first addition 10 of the potassium carbonate an increase of ~3% in the ethylene content of the $C_2$ total product in the tailgas was immediately observed (from 57% to 60%), which corresponded to a decrease in the ethane content from 43% to 40%. The effect continued until Synthol online catalyst removal and addition (SOLCRA technique) 12 was conducted on the reactor. Thereafter, the ethylene content of the $C_2$ total product in the tailgas decreased to values as low as 55%.

A second addition 14 of 175 kg potassium carbonate was performed three days later, and the effects were again immediate. The gain on ethylene content of the $C_2$ total product in the tailgas was about 4%, which later stabilized at 3% continuously until the reactor was shut down.

Figure 2:
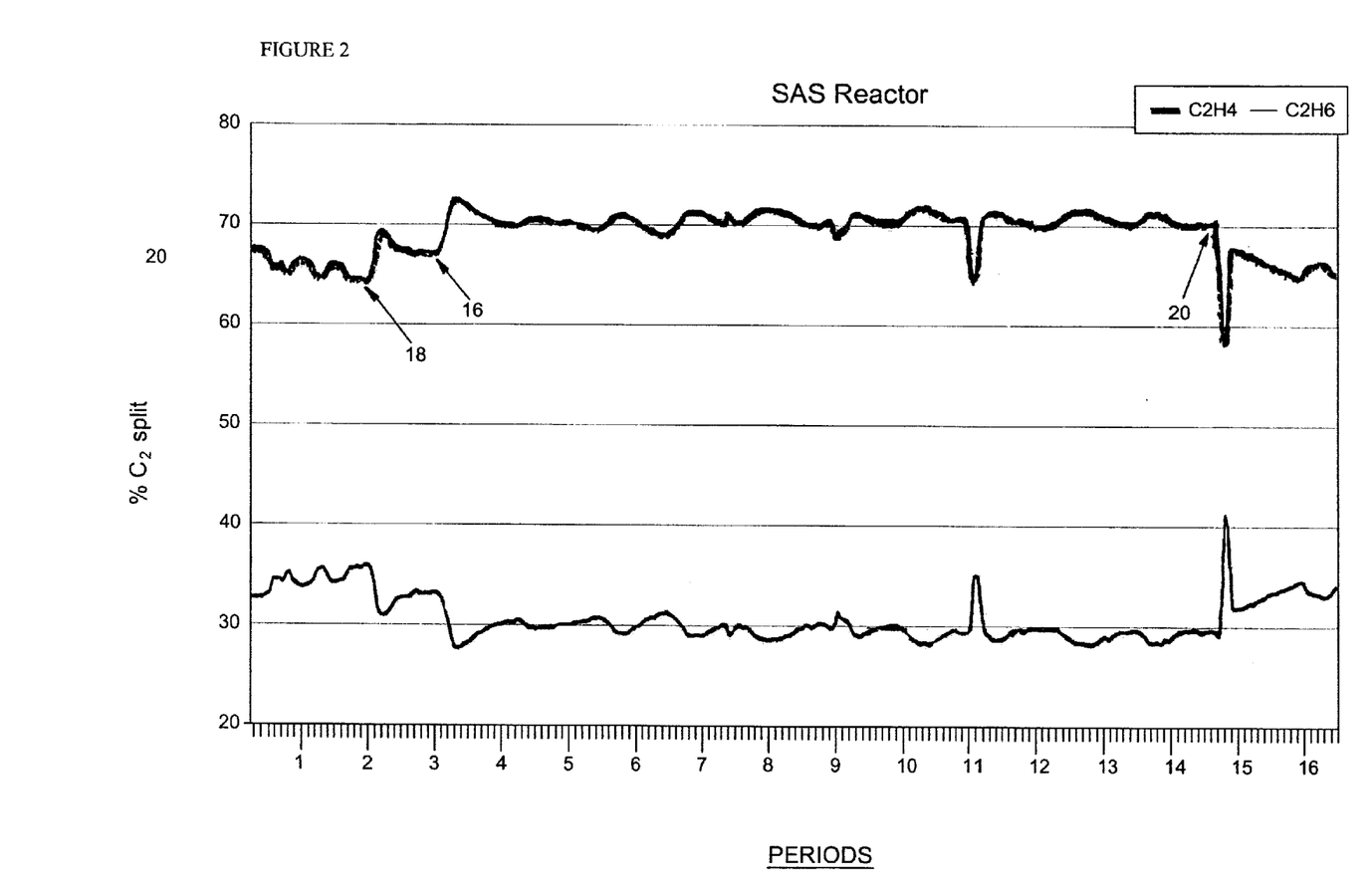
FIG. 2 shows a graphic representation of the $C_2$ total split of ethylene and ethane from a test similar to the test of FIG. 1 but conducted on a fixed fluidized bed reactor.
Figure 3:
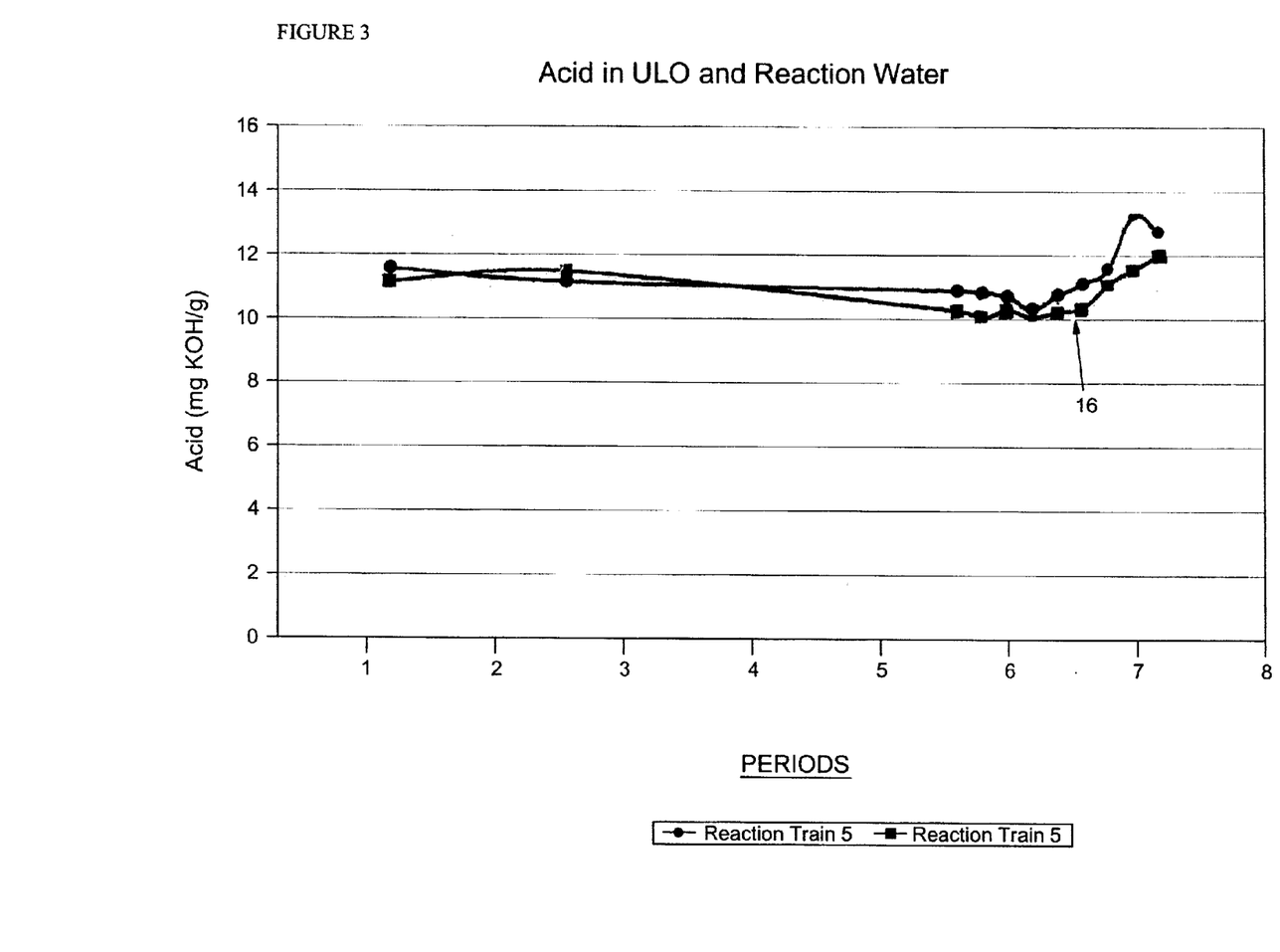
FIG. 3 shows a graphic representation of acids in an unstabilized light oil is fraction and in reaction water during the test of FIG. 2.

FIG. 2 shows the $C_2$ total split of ethylene and ethane from a test conducted on the SAS reactor, wherein the complementary effect of potassium online addition on these two products is illustrated. 220 kg potassium carbonate were added to the reaction medium at injection point 16, and the SOLCRA technique was conducted on the reactor at points 18 and 20. Visually, the profile depicts the ethylene content of the $C_2$ total product as a mirror image of that of ethane, i.e. an increase in ethylene is complemented by a corresponding decrease in ethane. This increase in the ethylene yield due to the loose injection of a potassium promoter is stable, and the ethylene selectivity does not show the normal decay that is observed after the normal online catalysts addition and removal procedures. The acids in the reaction water, as well as in the ULO fraction, also increased as a result of the injection of the potassium carrier into the reactor, as depicted in FIG. 3.

EXAMPLE 2

This example illustrates that the catalyst composition is the major variable that influences the Synthol process selectivities under standard operating conditions which include feed gas composition and feedrate, conversions, pressures and temperatures.

The selectivity factor (SF) is defined by an expression which combines the iron catalyst potassium oxide, alumina and silica compositions, with the exclusion of sodium oxide.

$$SF = \frac{(K_2O)}{(Al_2O_3 + SiO_2)} \quad (3)$$

This factor was used to investigate whether there exists any correlation between the selectivity profile of the various components of the product spectrum and the catalyst composition. The data parameters that were correlated were the selectivities for methane, ethylene/ethane, propylene/propane, butene/butane, $C_1$–$C_4$ paraffins and ULO acids.

The results, shown in FIGS. 4 to 10, suggest that the correlation between the selectivity factor and the Synthol reactor observed selectivities is prevalent. Despite the data scattering there exists a clear trend between the selectivity factor and the said parameters.

Figure 4:
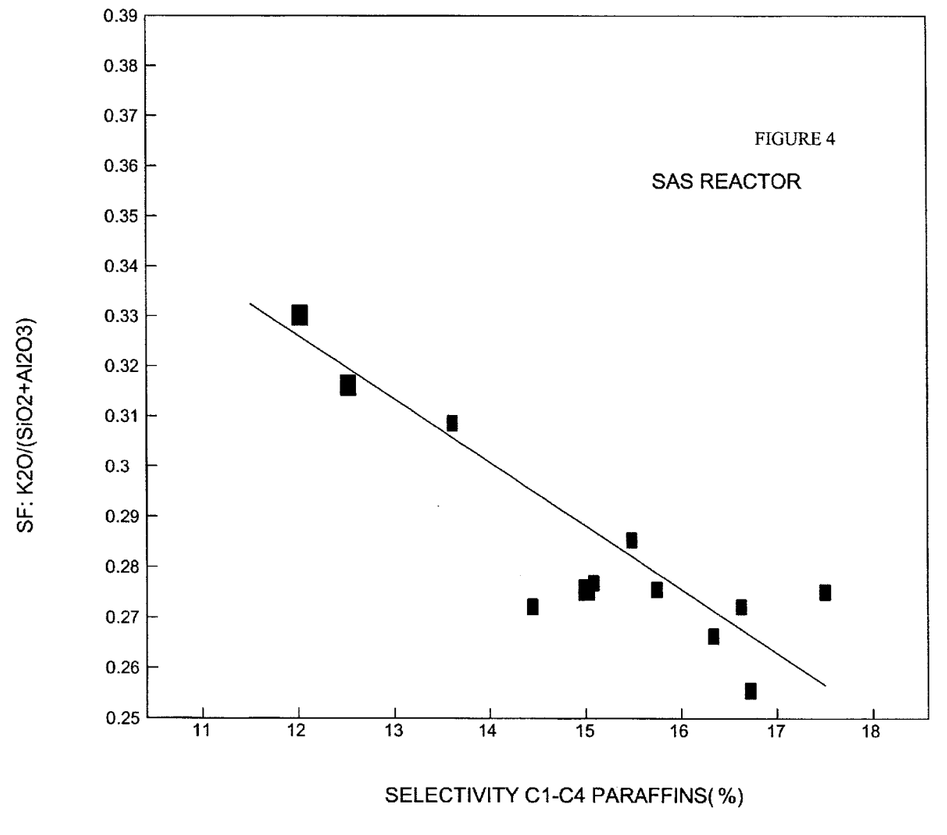
FIG. 4 shows a graphic representation of $C_1$–$C_4$ paraffin selectivity during the test of FIG. 2.
Figure 5:
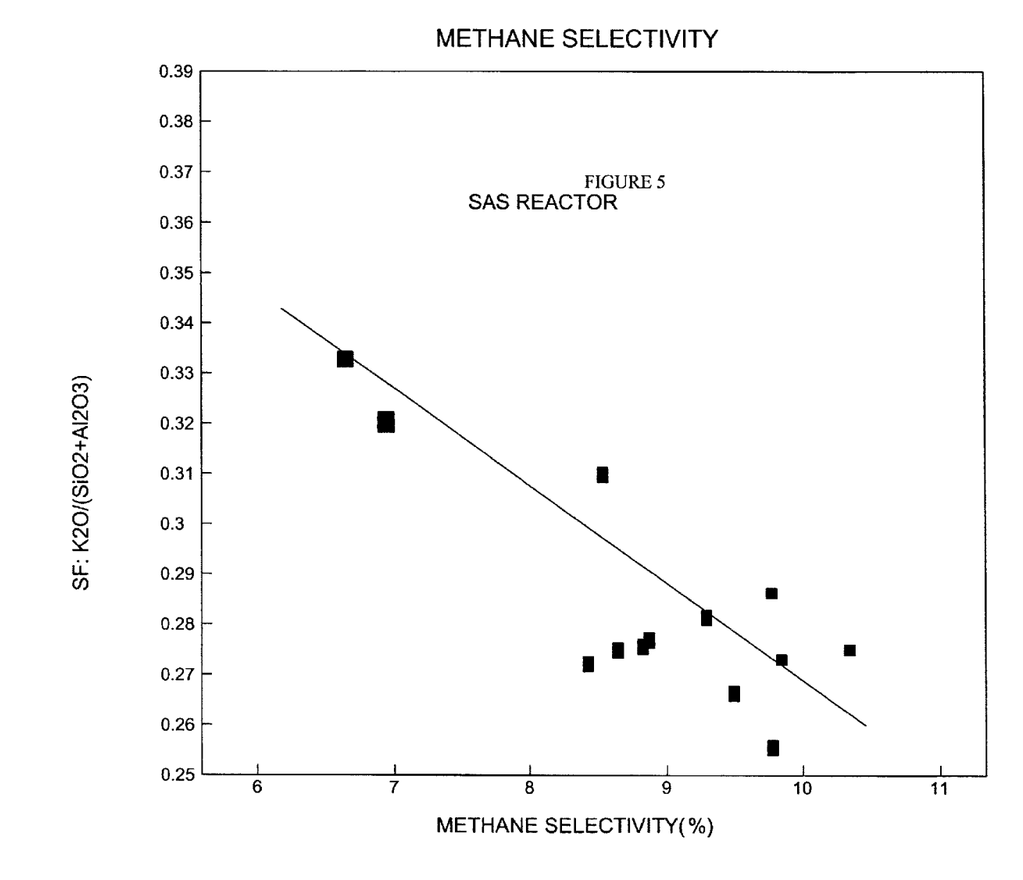
FIG. 5 shows a graphic representation of methane selectivity during the test of FIG. 2.
Figure 6:
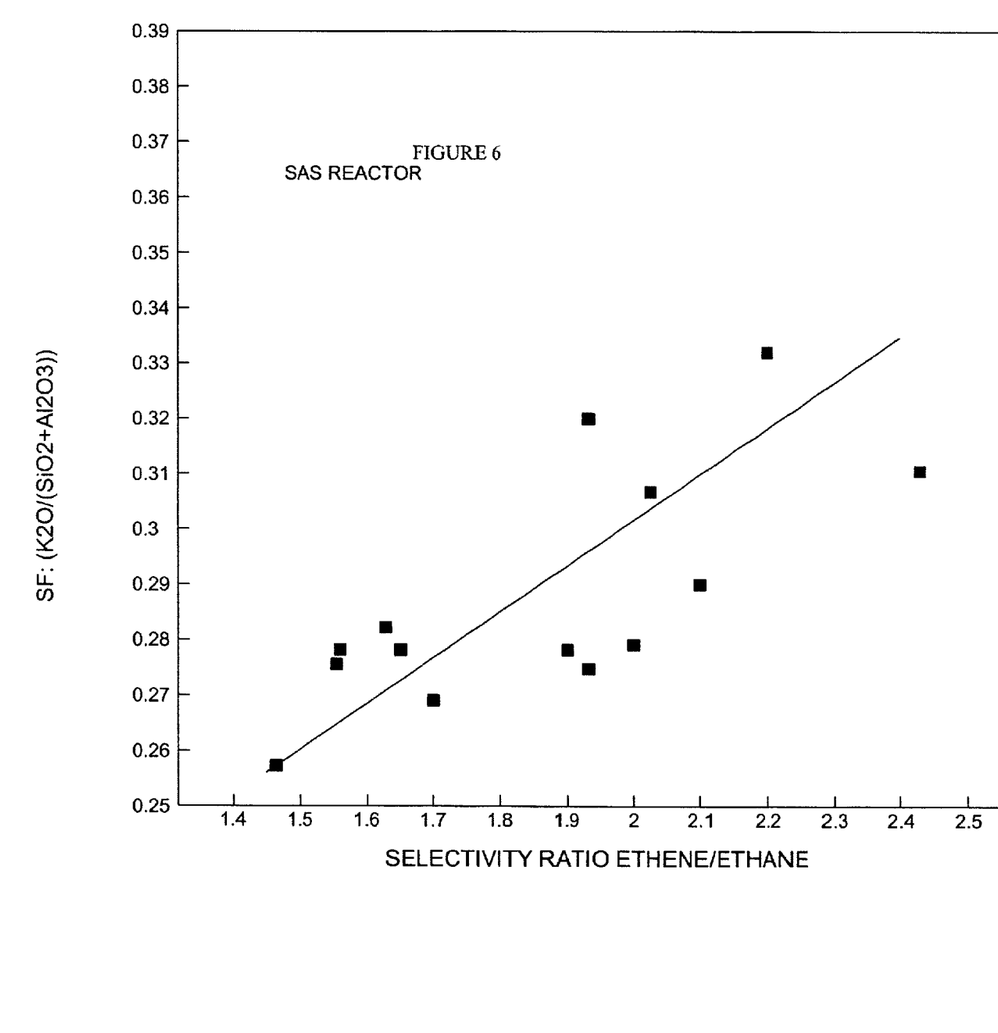
FIG. 6 shows a graphic representation of an ethene:ethane selectivity ratio of the test of FIG. 2.
Figure 7:
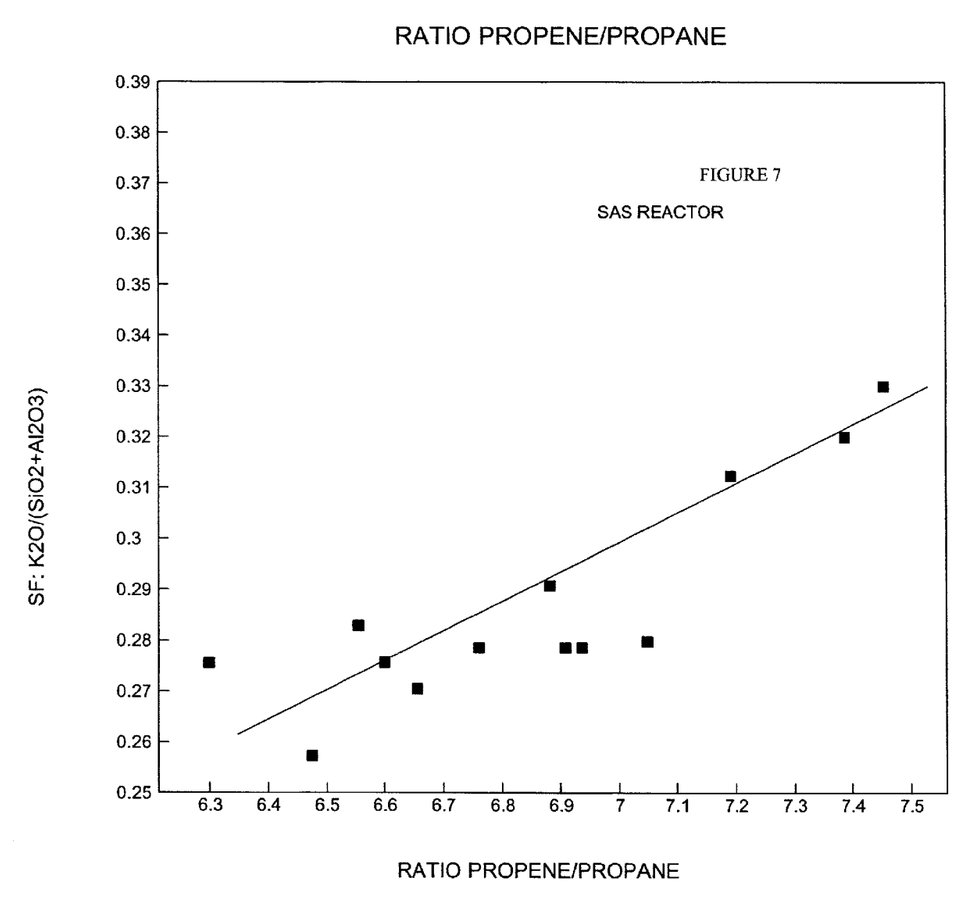
FIG. 7 shows a graphic representation of a propene:propane selectivity ratio of the test of FIG. 2.
Figure 8:
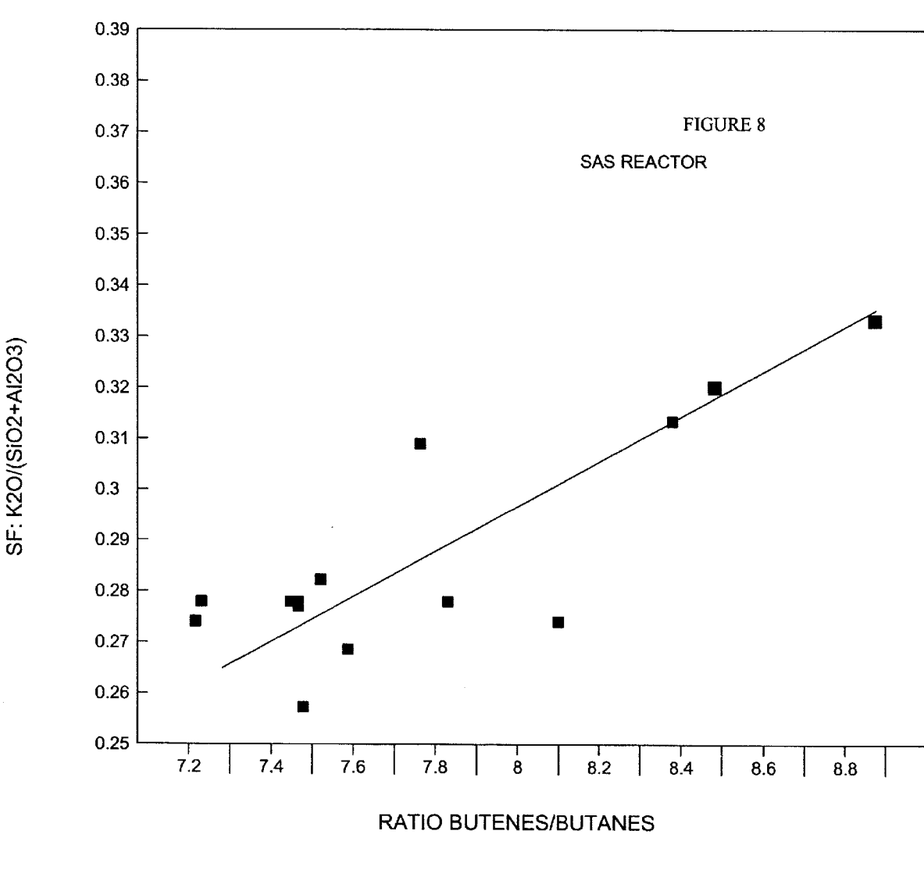
FIG. 8 shows a graphic representation of a butene:butane selectivity ratio of the test of FIG. 2.
Figure 9:
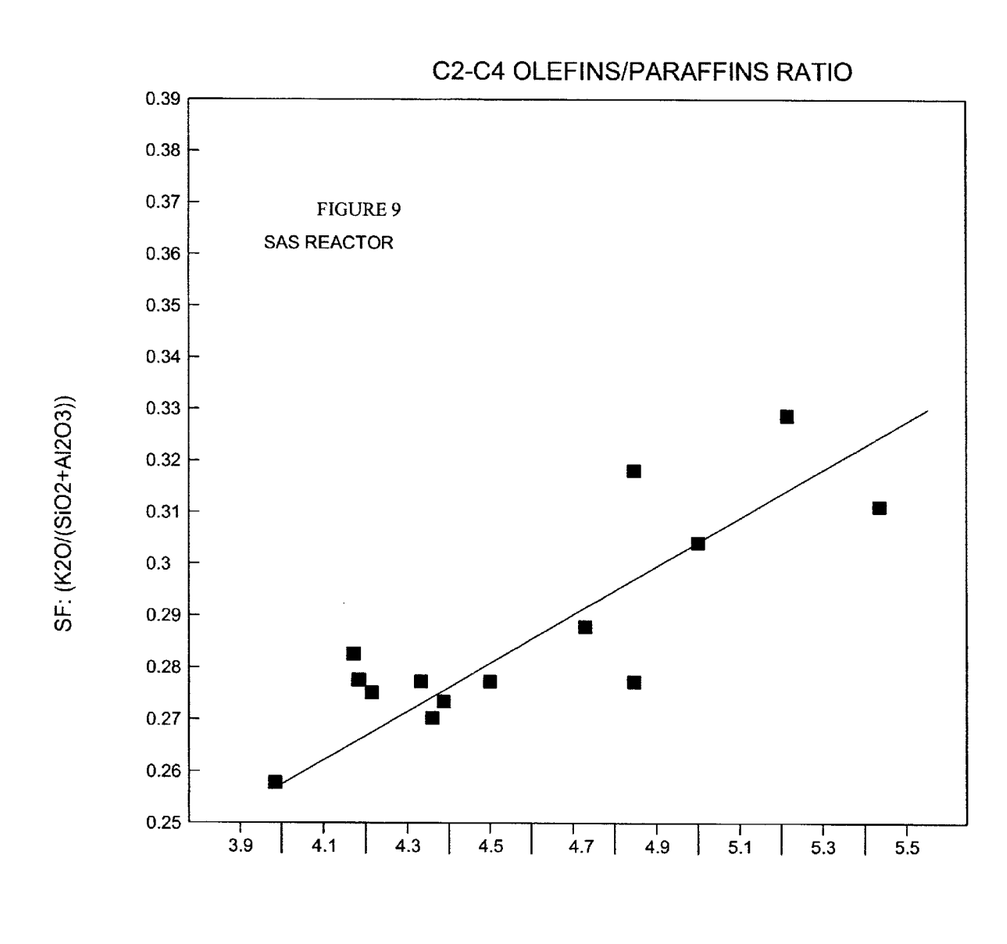
FIG. 9 shows a graphic representation of a $C_1$–$C_4$ olefin: paraffin selectivity ratio of the test of FIG. 2.

FIGS. 4 and 5 show the $C_1$–$C_4$ paraffins selectivities. The direction or the slope of the trends obtained indicate that as the potassium content of the catalyst composition decreases, the selectivity towards $C_1$–$C_4$ paraffins increases. The olefins:paraffins selectivity ratios for the $C_2$–$C_4$ hydrocarbons to are shown in FIGS. 6 to 8. The rest of the data followed the by-now-expected trend. The total $C_2$–$C_4$ olefin paraffin selectivity ratios (FIG. 9) compare favourably with those of the previous periods.

Figure 10:
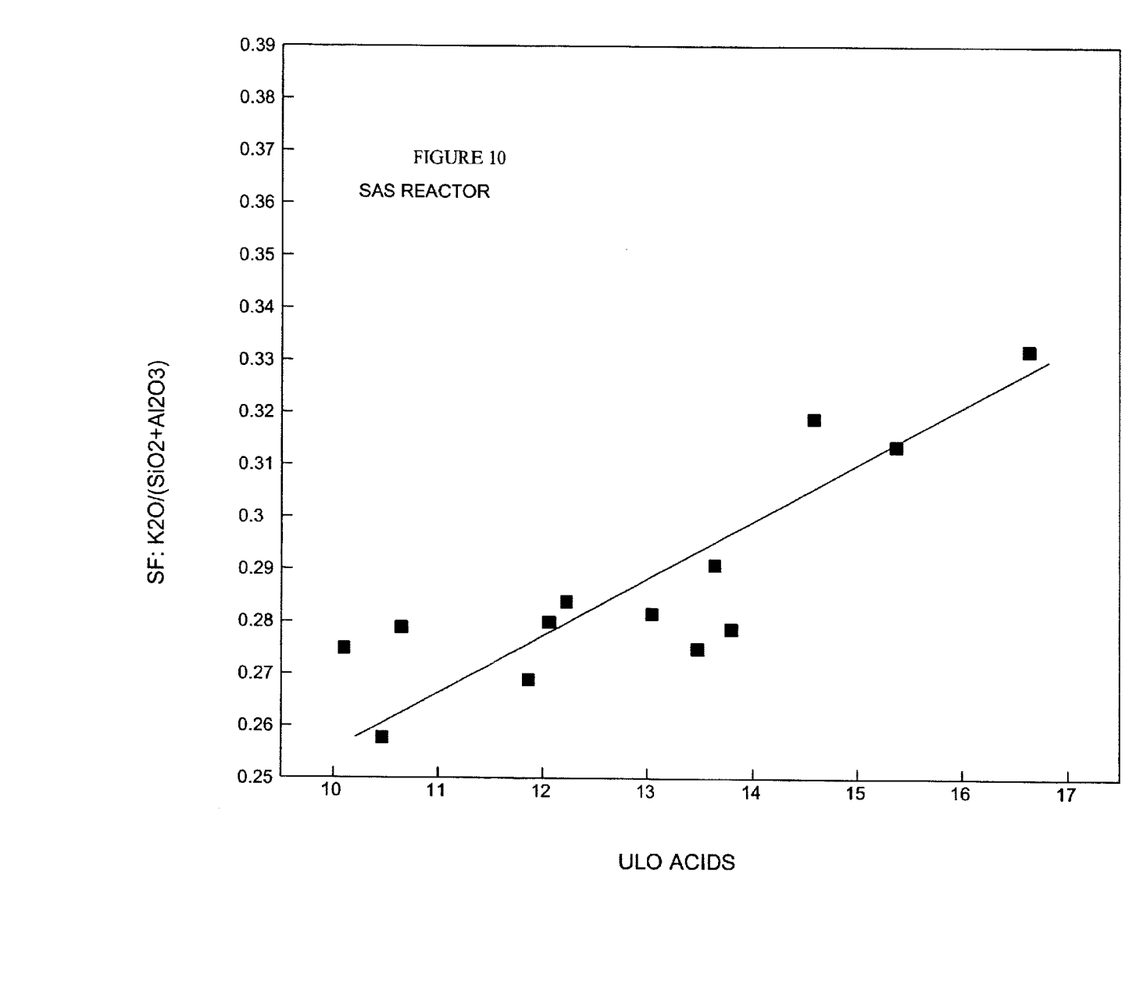
FIG. 10 shows a graphic representation of the selectivity factor on unstabilised light oil acids in the test of FIG. 2.

FIG. 10 shows the trend between the selectivities of the ULO acids and the selectivity factor.

EXAMPLE 3

This example illustrates that the selectivity factor may be accurately used to determine the amount of additional potassium promoter that is required in the Synthol Fischer-Tropsch reactor operating with an iron based catalyst in a fluidized mode, in order to predictably achieve a specific product olefin selectivity.

In an attempt to increase the $C_2$ olefin selectivity of a catalyst online, a certain amount of potassium promoter is added to alter the catalyst composition ratio ($Comp_r$) (determined using the above selectivity factor formula).

The general formula for the online addition of potassium (p) is therefore:

$$Required\ composition\ ratio = \frac{p + K_2O}{SiO_2 + Al_2O_3}$$

Expressed differently:

$$p = [ReqComp_r \times (SiO_2 + Al_2O_3) - K_2O]/0.68 \quad (4)$$

where $SiO_2$, $Al_2O_3$ and $K_2O$ refer to the composition of the spent catalyst that has the desirable $C_2$ selectivity. The term $ReqComp_r$ is used to indicate the ratio 1/SF which corresponds to a catalyst with the desired $C_2$ olefin selectivity. This formula applies specifically to $K_2CO_3$ as the promoter-carrying compound. If another promoter-carrying compound is used the formula will need to be modified to take into account the molecular weight of the specific compound.

To illustrate the effectiveness of this relation by way of an example, Table 1 shows the following date of spent Sasol Advanced Synthol catalyst compositions which are to be considered.

TABLE 1

| Component per 100 g Fe | Catalyst A | Catalyst B |
|---|---|---|
| $SiO_2$ | 1,03 | 1,015 |
| $Al_2O_3$ | 0,32 | 0,37 |
| $K_2O$ | 0,427 | 0,385 |
| Calculated $Comp_r$* (SF) | 0,316 | 0,278 |
| Ethylene/ethane (calculated selectivities) | 3,07 | 1,58 |
| Ethylene/ethane (In tailgas) | 2,52 | 1,53 |

*According to $K_2O/(SiO_2 + Al_2O_3)$

In order to improve the ethylene selectivity of catalyst B to that of catalyst A, using online promoter addition, application of formula (4) yields:

For $K_2O$:

$$p = 0.316(1.015 + 0.37) - 0.385$$

$$= 0.053\ g\ K_2O\ per\ 100\ g\ Fe$$

Therefore, an additional 0.053 g of $K_2O$ per 100 g Fe is required to lower the composition ratio ($Comp_r$) of catalyst B to that of the catalyst A giving the required ethylene olefin selectivity.

For $K_2SiO_3$:
1 g $K_2SiO_3$ forms 0.61 g $K_2O$ and 0.39 g $SiO_2$ $$Req\ comp = \frac{0.61p + K_2O}{(0.39p + 1)SiO_2 + Al_2O_3}$$

$$p = \frac{K_2O - Req\ comp\ (SiO_2 + Al_2O_3)}{0.39 \times Req\ comp - 0.61}$$

For $Req\ Comp = 0.316$ $$p = \frac{0.385 - 0.316(1.015 + 0.37)}{0.39 \times 0.316 - 0.61} = 0.10818\ g$$

i.e. addition of 0.10818 g $K_2SiO_3$ per 100 g Fe

Therefore the required catalyst composition is:

$SiO_2 = 1.015 + 0.10818 \times 0.39 = 1.05719$ g $Al_2O_3 = 0.37$ g $SiO_2 + Al_2O_3 = 1.427$ g $K_2O = 0.385 + 0.10818 \times 0.61 = 0.45099$ g thus $SF = \dfrac{0.45099}{1.0572 + 0.37}$ $= 0.316$ For $K_2CO_3$
1 g $K_2CO_3$ forms 0.68 g $K_2O$ $Req\ Comp = \dfrac{0.68p + K_2O}{SiO_2 + Al_2O_3}$ $p = \dfrac{Req\ Comp\ (SiO_2 + Al_2O_3) - K_2O}{0.68}$ e.g. $p = \dfrac{0.316(1.015 + 0.37) - 0.385}{0.68}$ $= 0.0774$ g $K_2CO_3$ i.e. addition of 0.0774 g $K_2CO_3$ per 100 g Fe
Therefore the required catalyst composition is:

$SiO_2 = 1.015$ g $Al_2O_3 = 0.37$ g $K_2O = 0.385 + 0.0774 \times 0.69 = 0.438$ g or $SF = \dfrac{0.438}{1.015 + 0.37}$ $= 0.316$ The invention is not limited to the precise constructional details as hereinbefore described. For example, the catalyst promoter need not be restricted to potassium carbonate or potassium silicate, and could be any similar substance or chemical equivalent which achieves the same or similar results. It will also be apparent to a person skilled in the art that equations other than the ones listed above may also be used to determine the selectivity factor. It is therefore to be understood that the method for calculating the selectivity factor is not to be limited to the equations as set out herein.

The applicant believes that the invention as illustrated and described is advantageous in that it provides a novel method for modifying, and thus controlling the selectivity profile of a Fischer-Tropsch synthesis process operating with a catalyst in a fluidized mode.

What is claimed is:

1. A method for control product selectivity for olefins of a Fischer-Tropsch synthesis process, the method comprising introducing into a Fisher-Tropsch reaction medium comprising a Fischer-Tropsch catalyst in a reactor, during the synthesis process, a catalyst promoter or catalyst promoter-containing compound, wherein the catalyst promoter or catalyst promotor-containing compound comprises an alkali and is in a form separate from a Fischer-Tropsch synthesis catalyst, so as to maintain catalyst activity in the reactor.

2. A method as claimed in claim 1, wherein the Fischer-Tropsch process is a High Temperature Fischer-Tropsch process.

3. A method as claimed in claim 1, wherein the catalyst promoter or catalyst promoter-containing compound is introduced into a fluidized bed Fischer-Tropsch reactor feedstream.

4. A method as claimed in claim 1, wherein the catalyst promoter is a promoter for an iron catalyst.

5. A method as claimed in claim 1, wherein the catalyst promoter-containing compound comprises an alkali oxide or an alkali salt.

6. A method as claimed in claim 1, wherein the catalyst promoter-containing compound is selected from the group consisting of potassium oxide, potassium carbonate, and potassium silicate.

7. A method as claimed in claim 1, wherein a product selectivity of olefins is increased compared to a product selectivity of paraffins by the introduction of the catalyst promoter or the catalyst promoter-containing compound during the synthesis process.

8. A method as claimed in claim 7, wherein a level of $C_2$–$C_4$ olefins in the reaction medium is increased.

* * * * *